United States Patent [19]

Yamada et al.

[11] Patent Number: 4,637,982
[45] Date of Patent: Jan. 20, 1987

[54] PROCESS FOR BIOLOGICAL PREPARATION OF AMIDES

[75] Inventors: Hideaki Yamada, 19-1, Kinomoto-Cho, Matsugasaki, Sakyo-Ku, Kyoto-Shi, Kyoto-Fu; Yoshiki Tani, Kyoto, both of Japan

[73] Assignees: Hideaki Yamada, Kyoto; Nitto Kagaku Kogyo Kabushiki Kaisha, Tokyo, both of Japan; a part interest

[21] Appl. No.: 527,579

[22] PCT Filed: Sep. 29, 1982

[86] PCT No.: PCT/JP82/00393
§ 371 Date: Jul. 5, 1983
§ 102(e) Date: Jul. 5, 1983

[87] PCT Pub. No.: WO83/01784
PCT Pub. Date: May 26, 1983

[30] Foreign Application Priority Data

Nov. 18, 1981 [JP] Japan .................. 56-184688

[51] Int. Cl.⁴ .................. C12P 13/02; C12P 1/04; C12N 9/78; C12R 1/38
[52] U.S. Cl. .................. 435/129; 435/170; 435/227; 435/228; 435/874
[58] Field of Search .............. 435/129, 170, 874, 227, 435/228

[56] References Cited

U.S. PATENT DOCUMENTS 4,001,081  1/1977  Commeyras et al. ............... 435/129

FOREIGN PATENT DOCUMENTS 0109083  5/1984  European Pat. Off. .
0133927  3/1985  European Pat. Off. .

OTHER PUBLICATIONS

Asano et al., Agric. Biol. Chem., 44(9), pp. 2251–2252, 1980.
Asano et al., Agricultural and Biological Chemistry, vol. 46, No. 5 (1982), pp. 1183–1189.
Arnaud et al., Agric. Biol. Chem., vol. 41, No. 11, (1977), pp. 2183–2191.

*Primary Examiner*—Robert J. Warden
*Assistant Examiner*—Patricia Kate White
*Attorney, Agent, or Firm*—Robert E. Burns; Emmanuel J. Lobato; Bruce L. Adams

[57] ABSTRACT

In a process for hydrating a nitrile having 2 to 4 carbon atoms by a microbiological treatment to convert the nitrile into the corresponding amide, it is possible to biologically prepare the corresponding amide effectively by utilizing a microorganism of the genus Pseudomonas which is capable of hydrating the nitrile to convert the same into the corresponding amide. In particular, it is possible to obtain acrylamides which are highly useful polymers by the very simple and energy-saving process in accordance with the present invention.

21 Claims, No Drawings

PROCESS FOR BIOLOGICAL PREPARATION OF AMIDES

TECHNICAL FIELD

The present invention relates generally to a process for hydrating lower aliphatic nitriles by a microbiological treatment to prepare the corresponding amides. More particularly, it relates to a process for biological preparation of amides characterized by the microorganisms used.

BACKGROUND ART

Lower aliphatic amides, for example, acrylamide, can be prepared by hydrating the corresponding nitriles, for example, acrylonitrile, and a method in which microorganisms are utilized for the hydration has been proposed, for instance, in Japanese Patent Laid-Open Publication No. 86186/1976 and Japanese Patent Publication No. 17918/1981.

DISCLOSURE OF THE INVENTION

Summary

The present invention relates to a process for biologically hydrating lower aliphatic nitriles by means of microorganisms of the genus Pseudomonas to prepare the corresponding amides.

Therefore, the process for biological preparation of amides according to the present invention which comprises hydrating nitriles having 2 to 4 carbon atoms by a microbiological treatment to convert the nitriles into the corresponding amides is characterized in that the microorganisms used are of the genus Pseudomonas and are capable of hydrating the nitriles to convert the same into the corresponding amides.

Meritorious effect

As will be noted from the examples which will be set forth hereinafter, the microorganisms used in the present invention have particularly remarkable acrylamide-forming ability and yet show substantially no capability of hydrolyzing acrylamide, which has once been formed, into acrylic acid. Thus, the solution obtained by the hydration reaction contains acrylamide in high concentration, whereby the recovery of acrylamide can be facilitated.

Further, the optimum temperature for the hydration reaction is ordinarily as low as 0° to 20° C., so that the process of this invention is advantageous from the viewpoint of economy of thermal energy.

DETAILED DESCRIPTION OF THE INVENTION

1. Nitriles To Be Treated

Nitriles to be hydrated in accordance with the present invention are those having 2 to 4 carbon atoms. Examples of such nitriles are acetonitrile, propionitrile, acrylonitrile, methacrylonitrile, n-butyronitrile, and isobutyronitrile. Among these nitriles, acrylonitrile is typical and can be hydrated with good results.

In the presence of the microorganisms to be used in this invention, nitriles having 5 or more carbon atoms or aromatic nitriles tend to be less easily hydrated than nitriles having 2 to 4 carbon atoms.

2. Biological Hydration Reaction

The microbiological hydration reaction of nitriles according to the present invention is not substantially different from the prior art methods mentioned hereinbefore except that specific species of microorganisms are used.

The term "hydration of nitriles by a microbiological treatment to convert the nitriles into the corresponding amides" as used herein is intended to cover both the case wherein microorganisms are cultured in the presence of nitriles and the case wherein nitriles are contacted with cultures obtained by culturing microorganisms, cells collected from the cultures, or cells which have been subjected to some treatment (such as ground cells or enzymes separated and extracted from cells). This term also refers to the case wherein cells or enzymes produced thereby are immobilized and utilized in the hydration reaction. In this connection, the biological hydration reaction of the present invention is considered to proceed by the aid of an enzyme (nitrile hydratase) produced by the microorganisms.

The culture of the microorganisms used in the present invention can be carried out by any method suitable for the desired purpose. For the culture media to be utilized, in general, those containing carbon sources such as glucose, maltose, and dextrins, nitrogen sources such as ammonium sulfate, ammonium chloride, and nitriles other than those to be hydrated, for example, isobutyronitrile in the case where acrylonitrile is hydrated, organic nutriment sources such as yeast extract, malt extract, peptone, and a meat extract, inorganic nutriment sources such as phosphates, magnesium, potassium, zinc, iron, and manganese, and the like are preferred.

The pH of the culture medium is of the order of 6 to 9, preferably of the order of 7 to 8, and the culturing temperature is of the order of 20° to 37° C., preferably about 25° to 30° C. By carrying out the culture aerobically under these conditions for about 2 to 3 days, sufficiently active cells can be produced in sufficient quantity.

The culture may be carried out in the presence of a nitrile to be hydrated (the nitrile concentration being about 0.5 to 2% by weight of the culture) as has been set forth earlier, but the hydration reaction is preferably accomplished by isolating cells from the culture (for example, by centrifugation), dispersing the cells in water, isotonic sodium chloride solution or like aqueous media, and adding thereto a nitrile to be hydrated.

In this preferred mode of the invention, the hydration of a nitrile is accomplished by reacting an aqueous dispersion containing 0.1 to 5% by weight of cells of a microorganism and 0.5 to 2% by weight of a nitrile at a temperature of the order of 0° to 20° C., preferably 0° to 5° C., and a pH of about 6 to 9, preferably 7 to 8, for a period of the order of 1 to 30 hours. It is desirable that the consumed nitrile be supplemented continuously or intermittently so that the nitrile concentration in the reaction solution will be maintained within the range specified above. In order to maintain the pH value within the specified range, it is preferable to employ an appropriate buffer system. The microorganisms used in the present invention have a poor capability to further hydrate the amides produced, but, when the pH of the reaction system becomes excessively acidic or alkaline, hydrolysis proceeds so that carboxylic acids, for instance, acrylic acid, tend to be formed. The reaction temperature in the above specified range is generally suitable, but temperatures not exceeding 5° C. are preferred in the case where the hydration reaction is carried out over a long period of time, e.g., for 5 hours or longer with the addition of nitrile.

After hydration is conducted for some period of time, the nitrile is converted into the corresponding amide -continued

| | | | |
|---|---|---|---|
| 8 | Utilization of citric acid | Simon's culture: + | Simon's culture: + |
| 9 | Utilization of ammonium salt: | ammonium salt: | |

EXAMPLE 1

(1) Culture

Strain B 23 was cultured under the following conditions.

| (1) | Culture Medium | |
|---|---|---|
| | Dextrin | 0.5% |
| | $K_2HPO_4$ | 0.2% |
| | $MgSO_4.7H_2O$ | 0.02% |
| | Isobutyronitrile | 0.2% |
| | NaCl | 0.1% |
| | pH | 7.0 |
| (2) | Cultural Conditions: 28° C./3 days | |

(2) Hydration of Acrylonitrile

Acrylonitrile was added intermittently to the thus obtained culture, which was utilized as an enzyme source without treatment, for hydration thereof.

The reaction was carried out at 0° to 4° C. from the time when acrylonitrile was added, and the addition of acrylonitrile was continued to cause the concentration of acrylonitrile to be 0.4 M.

About 100 g/l of acrylonitrile was produced 84 hours after the initiation of the reaction. The acrylamide yield was nearly 99%, and the quantity of acrylic acid formed as a by-product was only 0.4% of the acrylonitrile added.

The isolation of acrylamide from the reaction solution was accomplished by freeze-drying the solution, extracting the freeze-dried substance with methanol, and concentrating the methanol extract to form a precipitate of crystals. The crystals obtained were recrystallized from methanol, and colorless, sheet-like crystals were obtained and identified as acrylamide from the melting point and by elementary analysis, NMR an IR.

EXAMPLE 2

(1) Culture

The procedure of Example 1 was followed.

(2) Hydration of Acrylonitrile

Cells were separated from the culture obtained, washed with water, and dispersed in water (potassium phosphate buffer pH 7.0) in a quantity sufficient to reach a concentration of 20 mg/ml, based on the dry weight of the cells, to form a dormant cell dispersion to which acrylonitrile was added continuously for hydration thereof.

The reaction was carried out at 0° to 4° C., and acrylonitrile was added intermittently to cause the concentration of acrylonitrile to be 0.4 M.

200 g/l of acrylamide was produced substantially linearly 7.5 hours after the initiation of the reaction. The reaction seemed to proceed further but was terminated at this stage since the reaction solution became viscous.

The acrylamide yield was nearly 99%, and the quantity of acrylic acid formed as a by-product was only about 0.7% of the acrylonitrile added.

The acrylamide thus produced was collected and identified as such in the same manner as in Example 1.

EXAMPLE 3

The substrate specificity of a nitrile hydratase in strain B 23 was examined by the cell method.

(1) Culture of Cells

The procedure of Example 1 was followed.

(2) Hydration of Nitrile

Cells were separated from the culture obtained, washed with water, and subjected to reaction under the following conditions. The volume of the reaction solution was 1 ml.

| Substrate nitrile | 300 μmole |
|---|---|
| Potassium phosphate buffer | pH 7.0/100 μmole |
| Cell | 10 mg (as dry cell) |
| Temperature | 30° C. |
| Reaction time | 1 hour |

The results obtained were as tabulated below.

| | Amide-Forming Activity | |
|---|---|---|
| Test Nitrile | (unit/mg)* | (%) |
| Acetonitrile | 0.11 | 31 |
| Propionitrile | 0.41 | 117 |
| Acrylonitrile | 0.35 | 100 |
| Methacrylonitrile | 0.08 | 23 |
| n-Butyronitrile | 0.20 | 57 |
| Isobutyronitrile | 0.18 | 51 |

*unit/mg: The activity which enables 1 mg of a cell to form 1 μmole/min. of acrylamide was defined as "1 unit".

EXAMPLE 4

This example shows a comparison of the hydration reactions of strains B 23 and PS 1.

(1) Culture of Cells

Cells were cultured similarly as in Example 1 except that 0.01% of yeast extract was further added to the culture medium of Example 1.

(2) Hydration of Acrylonitrile

Cells were separated from the culture obtained, washed with water, and subjected to reaction under the following conditions. The volume of the reaction solution was 1 ml.

| Acrylonitrile | 300 μmole |
|---|---|
| Potassium phosphate buffer | pH 7.0/100 μmole |
| Cell | 10 mg (as dry cell) |
| Temperature | 15° C. |
| Reaction time | 2 and 4 hours |

The results obtained were as tabulated below.

| | Formation of Acrylamide (%) | |
|---|---|---|
| Strain | 2 hours | 4 hours |
| B 23 | 90 | 100 |
| PS 1 | 82 | 97 |

INDUSTRIAL APPLICABILITY

As has been stated above, the present invention, which is directed to a process for biological preparation of amides, provides a process for hydrating lower aliphatic nitriles by using specific microorganisms of the genus Pseudomonas to effectively convert the nitriles into the corresponding amides. Especially, the present invention ensures a very simple and energy-saving process for preparing acrylamides which are highly useful polymers.

We claim:

1. A process for hydrating a nitrile having 2-4 carbon atoms to the corresponding amide which comprises contacting a nitrile with a microorganism of the genus Pseudomonas which produces nitrile hydratase.

2. The process as claimed in claim 1, wherein the nitrile is added to a culture of the microorganism in order to convert the nitrile into the corresponding amide.

3. The process as claimed in claim 1, wherein the nitrile is added to an aqueous dispersion of cells separated from a culture of the microorganism in order to convert the nitrile into the corresponding amide.

4. The process as claimed in either claim 2 or claim 3, wherein the nitrile is added continuously or intermittently.

5. The process as claimed in claim 1, wherein the nitrile is acrylonitrile and the microorganism is *Pseudomonas chlororaphis* B 23 (FERM BP-187) or Pseudomonas sp. PS 1 (FERM BP-188).

6. The process as claimed in claim 5, wherein the microorganism is *Pseudomonas chlororaphis* B 23.

7. The process as claimed in claim 1, wherein nitrile consumed during the hydration is supplemented during the reaction so that the nitrile concentration is maintained within the range of about 0.5 to 2% by weight.

8. The process as claimed in claim 7, wherein the nitrile is acrylonitrile.

9. The process as claimed in claim 1 wherein the hydration is carried out at a pH of about 6 to 9 and substantially no hydrolysis of the amide to an acid takes place during the hydration.

10. The process as claimed in claim 1 wherein the process is carried out at a temperature of 0° to 20° C.

11. A process for the biological preparation of an amide having 2 to 4 carbon atoms by hydrating the corresponding nitrile which comprises treating the nitrile with a microorganism selected from the group consisting of *Pseudomonas chlororaphis* B 23 (FERM BP-187) and Pseudomonas sp. PS 1 (FERM BP-188).

12. The process as claimed in claim 11, wherein the nitrile is acrylonitrile.

13. The process as claimed in claim 11 wherein the microorganism is *Pseudomonas chloraphis* B 23.

14. A process for hydrating a nitrile having 2-4 carbon atoms to the corresponding amide which comprises contacting a nitrile with nitrile hydratase produced by a microorganism of the genus Pseudomonas.

15. The process as claimed in claim 14, wherein the nitrile is added continuously or intermittently.

16. The process as claimed in claim 14, wherein nitrile consumed during the hydration is supplemented during the reaction so that the nitrile concentration is maintained within the range of about 0.5 to 2% by weight.

17. The process as claimed in claim 14, wherein the hydration is carried out at a pH of about 6 to 9 and substantially no hydrolysis of the amide to an acid takes place during the hydration.

18. The process as claimed in claim 14 wherein acrylonitrile is converted to acrylamide.

19. The process as claimed in claim 14, wherein the process is carried out at a temperature of 0° to 20° C.

20. The process as claimed in claim 14 wherein the microorganism is *Pseudomonas chlororaphis* B 23 (FERM BP-187) or Pseudomonas sp. PS 1 (FERM BP-188).

21. A method for the preparation of acrylamide from acrylonitrile comprising contacting acrylonitrile with nitrile hydratase produced by a microorganism of the genus Pseudomonas.

* * * * *